(12) United States Patent
Weiland et al.

(10) Patent No.: US 6,242,385 B1
(45) Date of Patent: Jun. 5, 2001

(54) ENHANCEMENT OF SEED/FRUIT/NUT YIELDS FROM FLOWERING PLANTS

(75) Inventors: Robert Timothy Weiland; Richard John Strunk, both of Cheshire, CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 09/514,701

(22) Filed: Feb. 28, 2000

(51) Int. Cl.$^7$ .................................................. A01N 47/30
(52) U.S. Cl. .............................................................. 504/330
(58) Field of Search ................................................ 504/330

(56) References Cited

U.S. PATENT DOCUMENTS

| | | | |
|---|---|---|---|
| 2,514,916 | 7/1950 | Wachta | 182/2 |
| 2,547,734 | 4/1951 | Barager | 64/32 |
| 3,450,747 | 6/1969 | Smith et al. | 260/479 |
| 3,748,356 | 7/1973 | Wellinga et al. | 260/553 |
| 4,564,639 * | 1/1986 | Nagase et al. | 514/594 |
| 5,322,938 | 6/1994 | McPherson et al. | 536/24.1 |
| 6,057,370 * | 5/2000 | Weiland et al. | 514/594 |

* cited by examiner

*Primary Examiner*—S. Mark Clardy
(74) *Attorney, Agent, or Firm*—Raymond D. Thompson; Paul Grandinetti

(57) ABSTRACT

A method for increasing the seed/fruit/nut yield of a flowering plant is disclosed wherein the method comprises treating said plant with a phenylurea of the structure

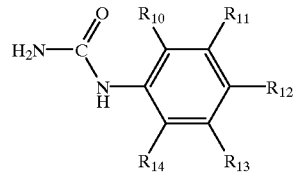

wherein $R_{10}$, $R_{11}$, $R_{12}$, $R_{13}$, and $R_{14}$ are independently selected from the group consisting of hydrogen, halogen, alkyl, alkenyl, alkoxy, aryl, aryloxy, nitro, cyano, alkylthio, alkylsulfinyl, alkylsulfonyl, and alkylenedioxy.

6 Claims, No Drawings

ENHANCEMENT OF SEED/FRUIT/NUT YIELDS FROM FLOWERING PLANTS

BACKGROUND OF THE INVENTION

1. Field of the Invention

The present invention is directed to agents for causing the enhancement of seed yield when applied to leguminous plants.

2. Description of Related Art

Diflubenzuron {N-(2,6-difluorobenzoyl)-N'-(4-chlorophenyl)urea} is an insect growth regulator that is active on many foliar feeding insects of soybeans, cotton, etc. It has previously been determined that the use of diflubenzuron can increase soybean seed yields, even when pest infestations are lower than the economically damaging threshold. This increase has been demonstrated when diflubenzuron was applied between the full bloom and beginning seed reproductive stages. It was unclear, however, as to how diflubenzuron could be increasing seed yield, since it binds readily to plant surfaces, is not considered to be translocated throughout the plant, and rarely is ever detected in the seed.

Diflubenzuron, which is commercially available as Dimilin® (Uniroyal Chemical Company, Inc.) belongs to the substituted 1-benzoyl-3-phenylurea family of pesticides and acts by interfering with the production/deposition of chitin, one of the main components of the insect exoskeleton.

After treatment with diflubenzuron, larvae have difficulties with the molting process, which results in an inability to cast off the old exoskeleton successfully and leads to the eventual death of the larvae. The mode of action of the diflubenzuron also gives rise to trans-ovarial effects by interfering with chitin deposition of the developing larva in the egg. Diflubenzuron exhibits long residual on plant tissue, but readily dissipates in soil or aqueous media. The compound is not considered systemic in the plant and therefore sucking insects are not usually affected.

Diflubenzuron provides control of a number of important pests in a variety of fruits, field crops, pasture and turf, horticulture and fish waters. Dimilin is labeled to control soybean pests that include velvetbean caterpillar (*Anticarsia gemmatalis*), Mexican bean beetle (*Epilachna varivestis*), green cloverworm (*Plathypena scabra*), beet armyworm (*Spodoptera exigua*), and fall armyworm (*Spodoptera frugiperda*). These insects can be considered economically damaging pests in soybeans grown in the southern United States; green cloverworm can occasionally cause significant damage in the northern United States.

The application of diflubenzuron to soybeans for controlling such pests can be made up to 21 days from harvest. A total of 0.062 lb a.i./acre/year (about 70 gm a.i./ha/year) can be applied. Typically, soybeans are treated for control of foliar feeding insects during the plant's reproductive period up to the point where damage will no longer limit final seed yield. The reproductive period can be segmented into different stages. Fehr et al. (*Stages of Soybean Development, Special Report* 80, 11 pages, Cooperative Extension Service, Iowa State University, Ames (1981)) describe eight "R" stages. They are RI, or beginning bloom; R2, or full bloom; R3, or beginning pod; R4, or full pod; R5, or beginning seed; R6, or full seed; R7, or beginning maturity; and R8, or full maturity.

These growth stages apply to both the determinate soybeans typically grown in the southern United States, and the indeterminate soybeans typically grown in the northern United States, except that R1 and R2 generally occur simultaneously in determinate varieties. Fehr et al also describe other differences in plant development between indeterminate and determinate varieties.

Up to 80% of the flowers formed on a soybean plant can be aborted as a flower or a pod (see van Schaik et al., *Agron. J* 50:192–197 (1958)) regardless of whether the plant is determinate or indeterminate. Additionally, van Schaik et al., supra, cite papers that describe other legumes (e.g., peanut, lima beans, white pea beans) and cotton as having a high number of flowers and/or fruit structures aborted.

U.S. Pat. No. 3,450,747 discloses that the compound N-(3,4-dichlorobenzoyl)-N'-(3,4-dichlorophenyl)urea has a herbicidal and/or insecticidal activity.

U.S. Pat. No. 3,748,356 discloses 2,6-dihalobenzoyl ureas that are said to be useful as insecticides. More specifically, the compounds are of the formula:

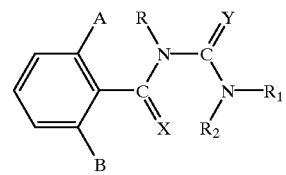

where

A is a hydrogen atom, a halogen atom, a methyl group or a methoxy group,

B also represents a hydrogen atom, a halogen atom, a methyl group or a methoxy group, with the proviso that A and B do not both represent a hydrogen atom, X and Y each represent an oxygen atom or a sulfur atom, R is a hydrogen atom, an alkyl group, a hydroxy group, an alkoxy group, an alkoxymethyl group, an acyl group or an alkoxycarbonyl group, $R_1$ is a hydrogen atom, an alkyl group which may be substituted with halogen, with alkoxy, with alkylthio or with cyano, a 1-cycloalkenyl group, a benzyl group which may be substituted with halogen, a hydroxy group, an alkoxy group, an acyl group, an alkoxycarbonyl group, an alkoxythiocarbonyl group, an alkylsulfonyl group or a phenylsulfonyl group, while furthermore R and $R_1$ together with the group

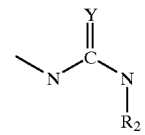

indicated in the above formula may form a ring system, and $R_2$ represents a substituted or non-substituted phenyl group or a pyridyl group which may be substituted with halogen, with nitrocyano or with halogenated alkyl.

If $R_2$ is a substituted phenyl group, the phenyl group contains at least one substituent chosen from the group consisting of:

(a) 1–3 halogen atoms, (b) 1–2 alkyl groups, possibly substituted with halogen, hydroxy, alkoxy, alkylthio, dialkyl amino, alkylsulphonyl and phenyl, (c) Tri- or tetramethylene, (d) A cycloalkyl group, possibly substituted with halogen or cyano,
(e) 1–2 nitro groups or cyano groups or alkoxy groups,
(f) A dioxymethylene or dioxy ethylene group,
(g) An acyl group, which may be substituted with halogen,
(h) An alkyl sulfonyl, phenyl sulfonyl, alkylthio, phenylthio or phenoxy group, which groups may be substituted with halogen,
(i) A sulfonamide group, which may be alkylated, and
(k) A phenyl group, which may be substituted with halogen, nitro, cyano and halogenated alkyl.

U.S. Pat. No. 6,057,370 is directed to a method of controlling insects of Lepidoptera on a genetically altered cotton plant having incorporated therein a gene derived from *Bacillus thuringiensis* (Bt) which codes for and expresses a protein having pesticide activity comprising the steps of applying to the foliage of said genetically altered cotton plant a pesticidally active amount of certain substituted benzoyl urea compounds, e.g., N-(2,6-difluorobenzoyl)-N'-(4-chlorophenyl)urea.

The disclosures of the foregoing are incorporated herein by reference in their entirety.

SUMMARY OF THE INVENTION

The present invention is directed to agents that cause the enhancement of seed/fruit/nut yield in flowering plants when the flowering plant is treated with a phenylurea compound. More specifically, the present invention is directed to agents that cause the enhancement of seed yield when certain phenylurea compounds, preferably substituted phenylurea compounds, e.g., 4-chlorophenyl)urea, or precursors thereof, are applied to flowering plants, especially soybeans. This mechanism for increasing yield is expected to be ubiquitous with other leguminous plants other than soybean, such as peanuts, lima beans, and navy beans, and even with cotton and flowering fruit/nut trees. Diflubenzuron, in the benzoylphenylurea chemistry class, is a slow-release molecule for the metabolite 4-chlorophenylurea. This metabolite is the agent for observed field increases from the application of diflubenzuron. For soybeans, the increase is a consequence of increased pod numbers on the plant that consequently give increased seed yield, since the seeds are no smaller in size or weight. Thus, application of diflubenzuron to any flowering plant could influence the number of flowers/fruiting structures retained.

More particularly, the present invention is directed to a method for increasing the seed/fruit/ nut yield of a flowering plant comprising treating said plant with a phenylurea of the structure

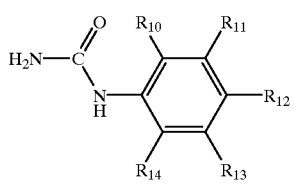

wherein
$R_{10}$, $R_{11}$, $R_{12}$, $R_{13}$, and $R_{14}$ are independently selected from the group consisting of hydrogen, halogen, alkyl, alkenyl, alkoxy, aryl, aryloxy, nitro, cyano, alkylthio, alkylsulfinyl, alkylsulfonyl, and alkylenedioxy.

DESCRIPTION OF THE PREFERRED EMBODIMENTS

As stated above, it is known in the art that use of diflubenzuron can increase soybean seed yields, even when pest infestations are lower than the economically damaging threshold, but it was unclear how diflubenzuron could be increasing seed yield since it binds readily to plant surfaces, is not considered to be translocated throughout the plant, and is rarely detected in the seed. Consequently, a field test was established to see if any of the metabolites of diflubenzuron could be the agent of the seed increase.

The main metabolites of diflubenzuron are 2,6-difluorobenzoic acid (DFBA) and 4-chlorophenylurea (CPU), whether occurring in water, soil, plants, or mammals. Both metabolites and diflubenzuron were foliarly applied to early podding soybean plants at Bethany, Conn., U.S.A. during 1998. Both diflubenzuron and CPU gave increased seed yield over the untreated control soybeans. The metabolite, DFBA, did not influence yield. Plants treated with either diflubenzuron or CPU had more pods and, thus, seed, when compared to the control. Neither number of seeds per pod nor seed size and weight were influenced by the treatment. Thus, it was concluded that CPU is the agent for the increased soybean seed yields noted from the application of diflubenzuron in the field. It was also concluded that diflubenzuron is a slow release compound for the active molecule, CPU.

As shown by the field test described above, CPU is an effective agent for increasing the seed yield of leguminous plants, e.g., soybeans. The structure of CPU is:

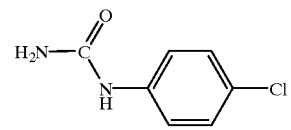

Those skilled in the art will readily recognize that substituents on the phenyl group other than, or in addition to, chlorine, and that would exert no negative property to the compound, could be employed in the practice of the present invention. Thus, according to the present invention, the compounds to be used to increase the seed/fruit levels of any flowering plant, including leguminous plants, are of the structure:

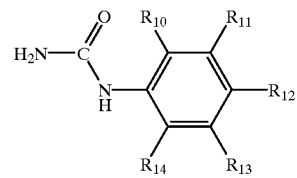

wherein
$R_{10}$, $R_{11}$, $R_{12}$, $R_{13}$, and $R_{14}$ are independently selected from the group consisting of hydrogen, halogen, alkyl, alkenyl, alkoxy, aryl, aryloxy, nitro, cyano, alkylthio, alkylsulfinyl, alkylsulfonyl, and alkylenedioxy. It is preferred that at least one of $R_{10}$, $R_{11}$, $R_{12}$, $R_{13}$, and $R_{14}$ be other than hydrogen.

Where $R_{10}$, $R_{11}$, $R_{12}$, $R_{13}$, and/or $R_{14}$ are halogen, they may be fluoro, chloro, bromo, iodo, or mixtures thereof Where $R_{10}$, $R_{11}$, $R_{12}$, $R_{13}$, and/or $R_{14}$ are alkyl, they are preferably alkyl of from one to twenty carbon atoms, e.g., an alkyl group (which term is intended to include functionalized alkyl and aralkyl groups), preferably having from 1 to about 20 carbon atoms. Thus, $R_{10}$, $R_{11}$, $R_{12}$, $R_{13}$, and/or $R_{14}$ can, for example, be methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, or isomers thereof, for example, isopropyl, isobutyl, sec-butyl, tert-butyl, 2-ethylhexyl, and the like.

It should also be noted here that any use of the term "alkyl" in the context of the compounds of this invention is deemed to include cycloalkyl and alkyl substituted cycloalkyl structures as well, for example, cyclopentyl, cyclohexyl, 4-methylcyclohexyl, and the like.

Additionally, the $R_{10}$, $R_{11}$, $R_{12}$, $R_{13}$, and/or $R_{14}$ alkyl group can be mono- or poly-substituted with, for example, functional groups or aryl groups. Such functional groups include, for example, halo, hydroxyl, aldehyde, carboxyl, sulfonyl, sulfinyl, thiol, amino, carboxamido and sulfenamido groups, and the like, either singly or in admixture. Aryl substituents include, for example, phenyl, naphthyl, biphenyl, azulenyl, anthracenyl, phenanthrenyl, and the like, which substituents may, also, be substituted to form, for example, tolyl, xylyl, anilino groups, and the like. Similarly, where $R_{10}$, $R_{11}$, $R_{12}$, $R_{13}$, and/or $R_{14}$ are aryl, they can be, for example, phenyl, naphthyl, biphenyl, azulenyl, anthracenyl, phenanthrenyl, and the like, which substituents may, also, be substituted to form, for example, tolyl groups, xylyl groups, anilino groups, and the like.

Where $R_{10}$, $R_{11}$, $R_{12}$, $R_{13}$, and/or $R_{14}$ are alkoxy or aryloxy, the alkyl or aryl moieties thereof will preferably be selected from those described above for alkyl and aryl, respectively.

Specifically preferred phenylureas for use in the practice of the present invention include, but are not limited to, phenylurea, 4-chlorophenylurea, 3-bromophenylurea, 2-fluorophenylurea, 4-iodophenylurea, 3,4-dichlorophenylurea, 2,6-difluorophenylurea, 2,4-dibromophenylurea, 4-chloro-2-fluorophenylurea, 2,4-difluorophenylurea, 3-chloro-4-fluorophenylurea, 3-tolylurea, 2-ethylphenylurea, 2,4,5-trichlorophenylurea, 2,6-dichloro-3-methylphenylurea, 4-t-butylphenylurea, 4-n-butylphenylurea, 2-isopropylphenylurea, 4-n-octylphenylurea, 4-dodecylphenylurea, 4-hexadecylphenylurea, 4-cyclohexylphenylurea, 2,3-dimethylphenylurea, 2,6-diethylphenylurea, 3,5-di-t-butylphenylurea, 4-allylphenylurea, 4-trifluoromethylphenylurea, 2-fluoro-4-methylphenylurea, 2,5-bis(trifluoromethyl)phenylurea, 2-fluoro-3-(trifluoromethyl)phenylurea, 3-chloro-4-methylphenylurea, 4-chloro-3-(trifluoromethyl)phenylurea, 3-methoxyphenylurea, 4-ethoxyphenylurea, 4-hexyloxyphenylurea, 4-phenoxyphenylurea, 4-[1,1'-biphenyl]ylurea, 3-fluoro-2-methoxyphenylurea, 4-methoxy-2-methylphenylurea, 2-methoxy-5-trifluoromethylphenylurea, 2-methoxy-5-trifluoromethoxyphenylurea, 3,4-dimethoxyphenylurea, 3,4,5-trimethoxyphenylurea, 2,3,4,5,6-pentafluorophenylurea, 4-methylthiophenylurea, 4-methylsulfinylphenylurea, 4-methylsulfonylphenylurea, 4-nitrophenylurea, 3,4-methylendioxyphenylurea, and the like.

The phenylureas employed in the practice of the present invention can be applied, per se, to flowering plants by methods well known to those skilled in the art. Alternatively, precursors of these phenylureas, i.e., benzoylureas, such as diflubenzuron, which will be metabolized in the plant to yield the phenylureas can be used. In many cases, this will be preferred, particularly where the plant is grown in regions where Lepidopteran pests are a problem, since application of the benzoylurea will provide the dual advantages of killing the pests and, simultaneously, increasing the yield of the desired seed. It should be understood, of course, that the precursors can advantageously be used in those regions where there is little or no Lepidopteran problem, since the crop yield will still be increased.

The benzoylurea precursors of the phenylureas of the present invention can be represented by the structural formula

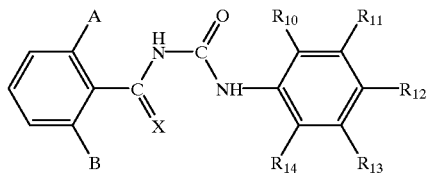

wherein
A and B are independently selected from the group consisting of hydrogen, halogen, methyl, and methoxy, X represents an oxygen atom or a sulfur atom, and $R_{10}$, $R_{11}$, $R_{12}$, $R_{13}$, and $R_{14}$ are as described above. Preferably, A and B are independently selected from the group consisting of chlorine, fluorine, and methyl and, more preferably, X is oxygen.

Diflubenzuron represents one of the most active structures. It belongs to the substituted 1-benzoyl-3-phenylurea family of pesticides, and has the following structure:

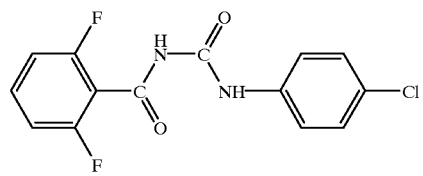

Other especially preferred benzoyl ureas that may be used as precursors of the phenylureas employed in the practice of the present invention include, but are not limited to:
N-(2,6-dichlorobenzoyl)-N'-(3,4-dichlorophenyl)urea,
N-(2,6-difluorobenzoyl)-N'-(3,4-dichlorophenyl)urea,
N-(2,6-dimethylbenzoyl)-N'-(3,4-dichlorophenyl)urea,
N-(2,6-dichlorobenzoyl)-N'-(4-chlorophenyl)urea,
N-(2,6-dimethylbenzoyl)-N'-(4-chlorophenyl)urea,
N-(2,6-dichlorobenzoyl)-N'-(2,4-dichlorophenyl)urea,
N-(2,6-dichlorobenzoyl)-N'-(4-cyclopropylphenyl)urea,
N-(2,6-dichlorobenzoyl)-N'-(3-chloro-4-iodophenyl)urea,
N-(2,6-dichlorobenzoyl)-N'-(3-chloro-4-bromophenyl)urea,
N-(2,6-dichlorobenzoyl)-N'-(4-isopropylphenyl)urea,
N-(2,6-dichlorobenzoyl)-N'-(3,4-dibromophenyl)urea,
N-(2,6-dichlorobenzoyl)-N'-(4-fluorophenyl)urea,
N-(2,6-dichlorobenzoyl)-N'-(3-trifluoromethylphenyl)urea,
N-(2,6-dichlorobenzoyl)-N'-(4-n-butylphenyl)urea,
N-(2,6-dichlorobenzoyl)-N'-(3-chloro-4-methylsulfonylphenyl)urea,
N-(2,6-dichlorobenzoyl)-N'-(4-t-butylphenyl)urea,
N-(2,6-dichlorobenzoyl)-N'-(3,4-difluorophenyl)urea,
N-(2,6-dichlorobenzoyl)-N'-(2,4-difluorophenyl)urea,
N-(2,6-dichlorobenzoyl)-N'-(4-bromophenyl)urea,
N-(2,6-dichlorobenzoyl)-N'-(2,5-difluoro-4-bromophenyl)urea,
N-(2,6-dichlorobenzoyl)-N'-(4-iodophenyl)urea,
N-(2,6-dichlorobenzoyl)-N'-(3-fluoro-4-chlorophenyl)urea,
N-(2,6-dichlorobenzoyl)-N'-(4-phenylphenyl)urea,
N-(2,6-dichlorobenzoyl)-N'-(4-cyanophenyl)urea,
N-(2,6-dichlorobenzoyl)-N'-(3-fluoro-4-bromophenyl)urea,
N-(2,6-dichlorobenzoyl)-N'-(3-fluoro-4-iodophenyl)urea,
N-(2,6-dichlorobenzoyl)-N'-(2-fluoro-4-iodophenyl)urea, N-(2,6-dichlorobenzoyl)-N'-(n-propylphenyl)urea,
N-(2,6-dichlorobenzoyl)-N'-(4-trifluoromethylphenyl)urea,
N-(2,6-dichlorobenzoyl)-N'-(3-cyclopropylphenyl)urea,
N-(2,6-dichlorobenzoyl)-N'-(2-methyl-4-chlorophenyl) urea,
N-(2,6-dichlorobenzoyl)-N'-(4-sec.butylphenyl)urea,
N-(2,6-dichlorobenzoyl)-N'-(4-isobutylphenyl)urea,
N-(2,6-dichlorobenzoyl)-N'-(4-ethylphenyl)urea,
N-(2,6-dichlorobenzoyl)-N'-(4-n-dodecylphenyl)urea,
N-(2,6-dichlorobenzoyl)-N'-(4-benzylphenyl)urea,
N-(2,6-dibromobenzoyl)-N'-(3,4-dichlorophenyl)urea,
N-(2,6-dichlorobenzoyl)-N'-(2,4,5-trichlorophenyl)urea,
N-(2,6-dichlorobenzoyl)-N'-(phenyl)urea,
N-(2,6-dichlorobenzoyl)-N'-(4-nitrophenyl)urea,
N-(2,6-difluorobenzoyl)-N'-(4-trifluoromethylphenyl)urea,
N-(2,6-difluorobenzoyl)-N'-(4-n-butylphenyl)urea,
N-(2,6-difluorobenzoyl)-N'-(4-t-butylphenyl)urea,
N-(2,6-difluorobenzoyl)-N'-(4-isopropylphenyl)urea,
N-(2,6-difluorobenzoyl)-N'-(3-fluoro-4-iodophenyl)urea,
N-(2,6-difluorobenzoyl)-N'-(3-fluoro-4-chlorophenyl)urea,
N-(2,6-difluorobenzoyl)-N'-(3-trifluoromethylphenyl)urea,
N-(2,6-difluorobenzoyl)-N'-(4-bromophenyl)urea,
N-(2,6-difluorobenzoyl)-N'-(4-fluorophenyl)urea,
N-(2,6-difluorobenzoyl)-N'-(4-thiomethylphenyl)urea, and the like.

Methods for the preparation of such precursors have been described, for example, in U.S. Pat. No. 3,748,356, the disclosure of which is hereby incorporated herein by reference.

The phenylureas of the present invention or their precursors may be formulated, as required, with a suitable carrier.

Suitable carriers for the present compositions are wide ranging. The carrier may be a solid, for example, finely divided particulate solids, granules, pellets, wettable powders, soluble powders, and the like. Among the solid carriers within the contemplation of the present invention are such organic and inorganic materials as attapulgite clay, sand, vermiculite, corn cob, activated carbon, and mineral silicates. Among the mineral silicates preferred for use in the composition of the present invention are mica, talc, pyrophyllite, clays, and the like.

A solid composition may be prepared from a solid carrier, such as one of those described immediately above. In that case, the active ingredient is impregnated onto the solid carrier. Alternatively, the active ingredient may be formulated into a wettable powder by grinding it into a fine powder and mixing it with the solid carrier to which a surface active dispersing agent has been added. The wettable powder is then dispersed in water and applied as a dispersion.

Indeed, the above described dispersion is representative of a composition that may be classified as a liquid composition. In addition to liquid dispersions, the liquid composition may be in the form of a solution or an emulsion. In the case of a liquid solution, the active ingredient is dissolved in an aqueous or organic solvent. In most cases the solvent, which acts as the carrier, is organic. In addition to aromatic hydrocarbons, such as toluene and xylene, other preferred solvents include such organic compounds as acetone, methanol, isopropanol, t-butyl alcohol, cyclohexanone, dioxane, dimethylformamide, dimethyl sulfoxide, ethylene dichloride, diacetone alcohol, and N-methylpyrrolidone.

A water emulsion, another preferred embodiment of a liquid composition within the contemplation of the present invention, is prepared from a solution, as described above, to which a surface active agent is added. Surface active agents suitable for use in forming an emulsion with the contemplation of this invention are known to those skilled in the art. *McCutcheon's Detergents and Emulsifiers,* Allured Publishing Corp., Ridgewood, N.J. (1970); U.S. Pat. No. 2,514,916 at columns 2 to 4; and U.S. Pat. No. 2,547,734, at columns 3 and 4 provide detailed examples of such surface active agents for this purpose. As indicated in these references, the surface active agent may be anionic, non-ionic, or cationic.

In yet another embodiment, the carrier may be an aerosol. To prepare an aerosol, the active ingredient is dissolved in a first solvent. This first solvent is conventional is the sense that although it is volatile, it is not highly volatile. This solution is then admixed with a highly volatile solvent, a so-called liquid aerosol carrier. The aerosol carrier is liquid only under elevated pressure. At ambient temperature and pressure, the aerosol carrier is a gas.

The active ingredient is typically formulated at weight percentages of from 10 to 90 percent, preferably 20 to 80 percent, and most preferably at 25 to 60 percent, with the remainder being carriers described in the section just above. This formulated product is then further diluted with water to create the appropriate dilution to be applied in the field at a rate of from about 0.01 gram of active ingredient (a.i.) per hectare (g/ha) to about 500 g of a.i./ha, preferably 0.1 to 400 g of a.i./ha and most preferably 1 to 300 g of a.i./ha.

The advantages and the important features of the present invention will be more apparent from the following example.

EXAMPLE

Diflubenzuron is typically sprayed during the period of R2 through R5 for controlling foliar feeding insects. An application of diflubenzuron at 0.031 lb. a.i./acre (35 gm a.i./ha) to flowering soybeans can increase seed yield of both determinate and indeterminate soybeans even though insects are not consistently present at yield limiting levels. It was considered that the increase was a result of more pods, and thus more seed, per plant. Other traits that could have resulted in an increase in seed yield are more seed per pod, heavier/larger seed, or a combination of two or more of the foregoing.

A field evaluation was established at Bethany, Conn. in 1998 to characterize the nature of the increase in yield from an application (0.031 lb. a.i./acre) (35 gm a.i./ha) of diflubenzuron at beginning to late pod growth stage. Additionally, the two main metabolites of diflubenzuron, 2,6-difluorobenzoic acid (DFBA) and 4-chlorophenylurea (CPU), were included in the evaluation. Molecular equivalent rates to diflubenzuron for the metabolites, 10-fold less, and 100-fold less were sprayed to early vegetative soybeans to assess any phytotoxicity. The molecular equivalent CPU rate of 0.017 lb a.i./acre (19 gm a.i./ha) was not phytotoxic and, thus, was used in the evaluation of reproductive soybeans. Since 0.014 lb a.i./acre (16 gm a.i./ha) of DFBA gave spotted chlorosis/necrosis to leaves sprayed and 0.0014 lb a.i./acre (1.6 gm a.i./ha) did not, the latter was used in the reproductive soybean evaluation.

The indeterminate variety "Chapman" was planted. Plots were single rows of approximately six meters in length. Rows were spaced 1.22 meters apart.

A randomized complete block statistical design was used for the four treatments (an untreated control was included), with six replications.

At field maturity, approximately five meters of row was harvested for plot yield. One meter of the five was used to characterize the nature of increase in yield for the treatments. The was no significant foliage feeding by any insect on the canopy during the duration of the trial. The results are given in Table 1.

TABLE 1

The Effect of Diflubenzuron, DFBA, and CPU on Soybean Seed Yield and Components of Yield at Bethany, CT During 1998 When Applied at the R3.2 Growth Stage

| Treatment | Plot Yield (kg/m) | 1 Meter Yield (kg/m) | Average Seed Wt. | Pods per Meter | Seeds per Meter | Seeds per Pod |
|---|---|---|---|---|---|---|
| Untreated Control | 0.373 | 0.395 | 0.200 | 757 | 1975 | 2.53 |
| Diflubenzuron @ 35 gm a.i./ha | 0.405 | 0.436 | 0.206 | 823 | 2127 | 2.54 |
| DFBA @ 1.6 gm a.i./ha | 0.377 | 0.391 | 0.202 | 755 | 1939 | 2.57 |
| CPU @ 19 gm a.i./ha | 0.417 | 0.451 | 0.206 | 835 | 2182 | 2.60 |
| LSD$_{0.05}$ | 0.031 | 0.043 | N.S. | 73 | 206 | N.S. |

N.S. = Not Significantly Different

Plot yield was increased eight and twelve percent over the untreated control with diflubenzuron and CPU, respectively, in this evaluation. Yield from the one meter portion of the row gave respective increases of 10 and 14% for these treatments. There were corresponding increases in pod and seed number with these treatments. Neither seed weight nor number of seed per pod was altered by the application of the treatments to the soybeans. These results indicate that the metabolite of diflubenzuron, CPU, is the agent responsible for the observed increase in soybean yield from a foliar application to soybeans in the reproductive stage. The nature of the increase is through additional flowers/pods maintained on the soybean plant. Diflubenzuron appears to be a slow release compound for the active molecule.

In view of the many changes and modifications that can be made without departing from principles underlying the invention, reference should be made to the appended claims for an understanding of the scope of the protection afforded the invention.

What is claimed is:

1. A method for increasing the seed yield of a leguminous plant comprising applying directly to the foliar portions of the plant during the plant's reproductive period a phenylurea of the structure

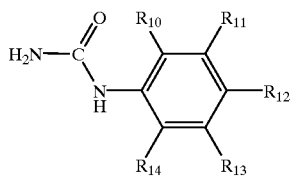

wherein
$R_{10}$, $R_{11}$, $R_{12}$, $R_{13}$, and $R_{14}$ are independently selected from the group consisting of hydrogen, halogen, alkyl, alkenyl, alkoxy, aryl, aryloxy, nitro, cyano, alkylthio, alkylsulfinyl, alkylsulfonyl, and alkylenedioxy.

2. The method of claim 1 wherein at least one of $R_{10}$, $R_{11}$, $R_{12}$, $R_{13}$, and $R_{14}$ is other than hydrogen.

3. The method of claim 1 wherein the leguminous plant is soybean.

4. The method of claim 1 wherein the phenylurea is selected from the group consisting of phenylurea, 4-chlorophenylurea, 3-bromophenylurea, 2-fluorophenylurea, 4-iodophenylurea, 3,4-dichlorophenylurea, 2,6-difluorophenylurea, 2,4-dibromophenylurea, 4-chloro-2-fluorophenylurea, 2,4-difluorophenylurea, 3-chloro-4-fluorophenylurea, 3-tolylurea, 2-ethylphenylurea, 2,4,5-trichlorophenylurea, 2,6-dichloro-3-methylphenylurea, 4-t-butylphenylurea, 4-n-butylphenylurea, 2-isopropylphenylurea, 4-n-octylphenylurea, 4-dodecylphenylurea, 4-hexadecylphenylurea, 4-cyclohexylphenylurea, 2,3-dimethylphenylurea, 2,6-diethylphenylurea, 3,5-di-t-butylphenylurea, 4-allylphenylurea, 4-trifluoromethylphenylurea, 2-fluoro-4-methylphenylurea, 2,5-bis(trifluoromethyl)phenylurea, 2-fluoro-3-(trifluoromethyl)phenylurea, 3-chloro-4-methylphenylurea, 4-chloro-3-(trifluoromethyl)phenylurea, 3-methoxyphenylurea, 4-ethoxyphenylurea, 4-hexyloxyphenylurea, 4-phenoxyphenylurea, 4-[1,1'-biphenyl]ylurea, 3-fluoro-2-methoxyphenylurea, 4-methoxy-2-methylphenylurea, 2-methoxy-5-trifluoromethylphenylurea, 2-methoxy-5-trifluoromethoxyphenylurea, 3,4-dimethoxyphenylurea, 3,4,5-trimethoxyphenylurea, 2,3,4,5,6-pentafluorophenylurea, 4-methylthiophenylurea, 4-methylsulfinylphenylurea, 4-methylsulfonylphenylurea, 4-nitrophenylurea, and 3,4-methylenedioxyphenylurea.

5. The method of claim 1 wherein the phenylurea is 4-chlorophenylurea.

6. The method of claim 1 wherein the phenylurea is applied in the field at a rate of from about 0.01 gram to about 500 grams of active ingredient per hectare.

* * * * *